(12) United States Patent
Hanlon et al.

(10) Patent No.: US 8,361,070 B2
(45) Date of Patent: Jan. 29, 2013

(54) NON-STICK BIPOLAR FORCEPS

(75) Inventors: Matthew A. Hanlon, O'Fallon, MO (US); James C. Easley, Cottleville, MO (US); Robert F. Spetzler, Paradise Valley, AZ (US)

(73) Assignee: Synergetics, Inc., O'Fallon, MO (US)

( * ) Notice: Subject to any disclaimer, the term of this patent is extended or adjusted under 35 U.S.C. 154(b) by 1708 days.

(21) Appl. No.: 11/676,340

(22) Filed: Feb. 19, 2007

(65) Prior Publication Data

US 2008/0200914 A1   Aug. 21, 2008

(51) Int. Cl.
*A61B 18/14* (2006.01)

(52) U.S. Cl. .............................. 606/51; 606/48; 606/52

(58) Field of Classification Search .................. 606/48, 606/51–52
See application file for complete search history.

(56) References Cited

U.S. PATENT DOCUMENTS

| | | | |
|---|---|---|---|
| 3,100,489 A * | 8/1963 | Bagley | 606/42 |
| 5,196,009 A | 3/1993 | Kirwan, Jr. | |
| 5,643,256 A | 7/1997 | Urueta | |
| 5,693,052 A | 12/1997 | Weaver | |
| 5,697,926 A | 12/1997 | Weaver | |
| 5,891,142 A * | 4/1999 | Eggers et al. | 606/51 |
| 6,059,783 A | 5/2000 | Kirwan, Jr. | |
| 6,293,946 B1 * | 9/2001 | Thorne | 606/48 |
| 6,749,610 B2 * | 6/2004 | Kirwan et al. | 606/51 |
| 2005/0283149 A1 * | 12/2005 | Thorne et al. | 606/48 |
| 2006/0276785 A1 | 12/2006 | Asahara et al. | |

FOREIGN PATENT DOCUMENTS

EP   1709923   * 11/2006

* cited by examiner

*Primary Examiner* — Linda Dvorak
*Assistant Examiner* — Jaymi Della
(74) *Attorney, Agent, or Firm* — Joseph M. Rolnicki; Evans & Dixon, LLC

(57) ABSTRACT

Disposable, bipolar electrosurgical forceps are designed to prevent the sticking of body tissue to the tips of the forceps and include a pair of electrode arms having lengths with opposite proximal and distal ends, with thin layers of biocompatible metal on the forceps arm distal ends and bipolar electrical conductors permanently secured to the forceps arm proximal ends.

17 Claims, 3 Drawing Sheets

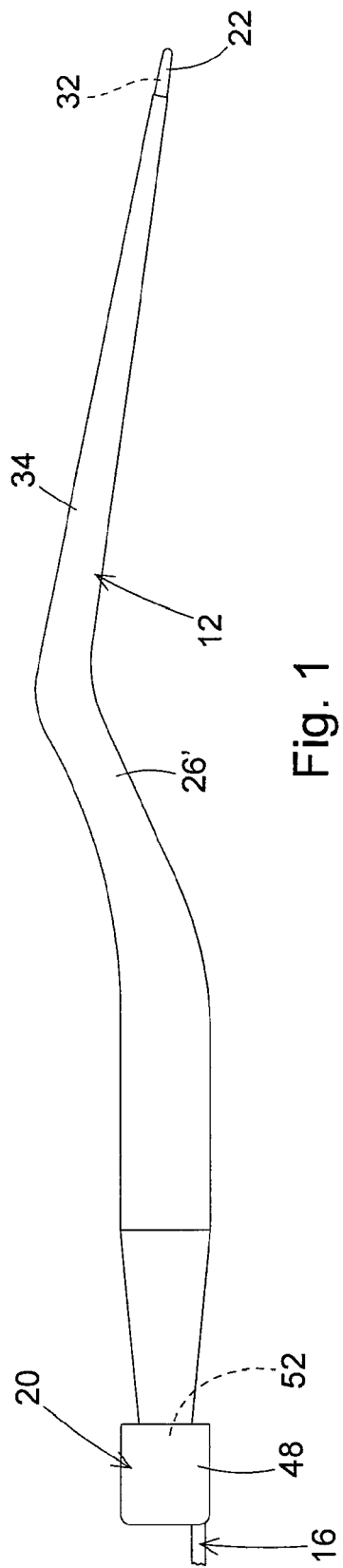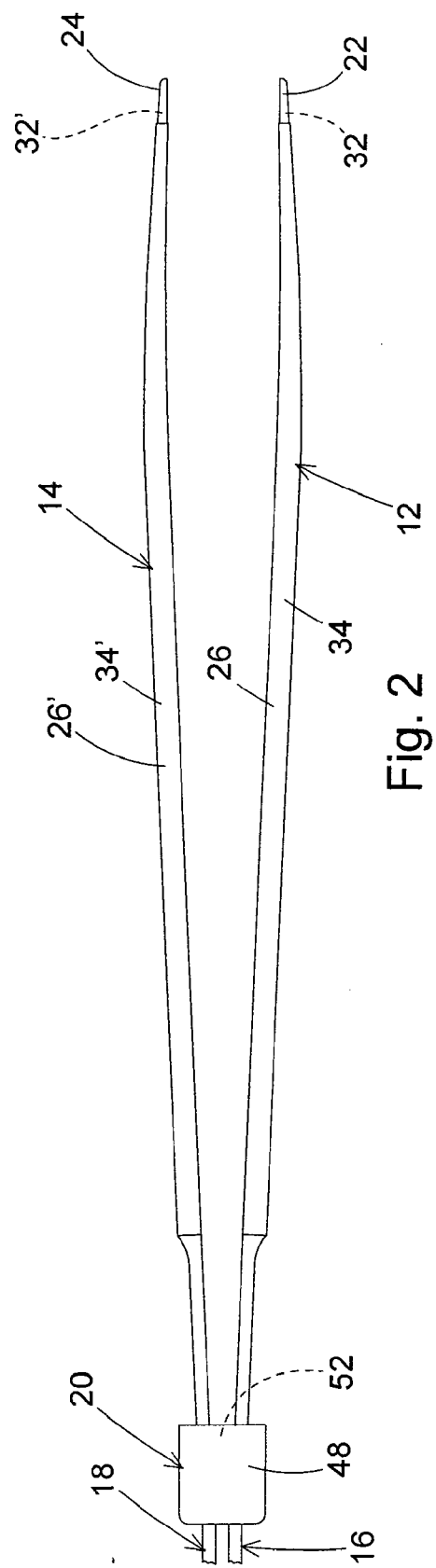

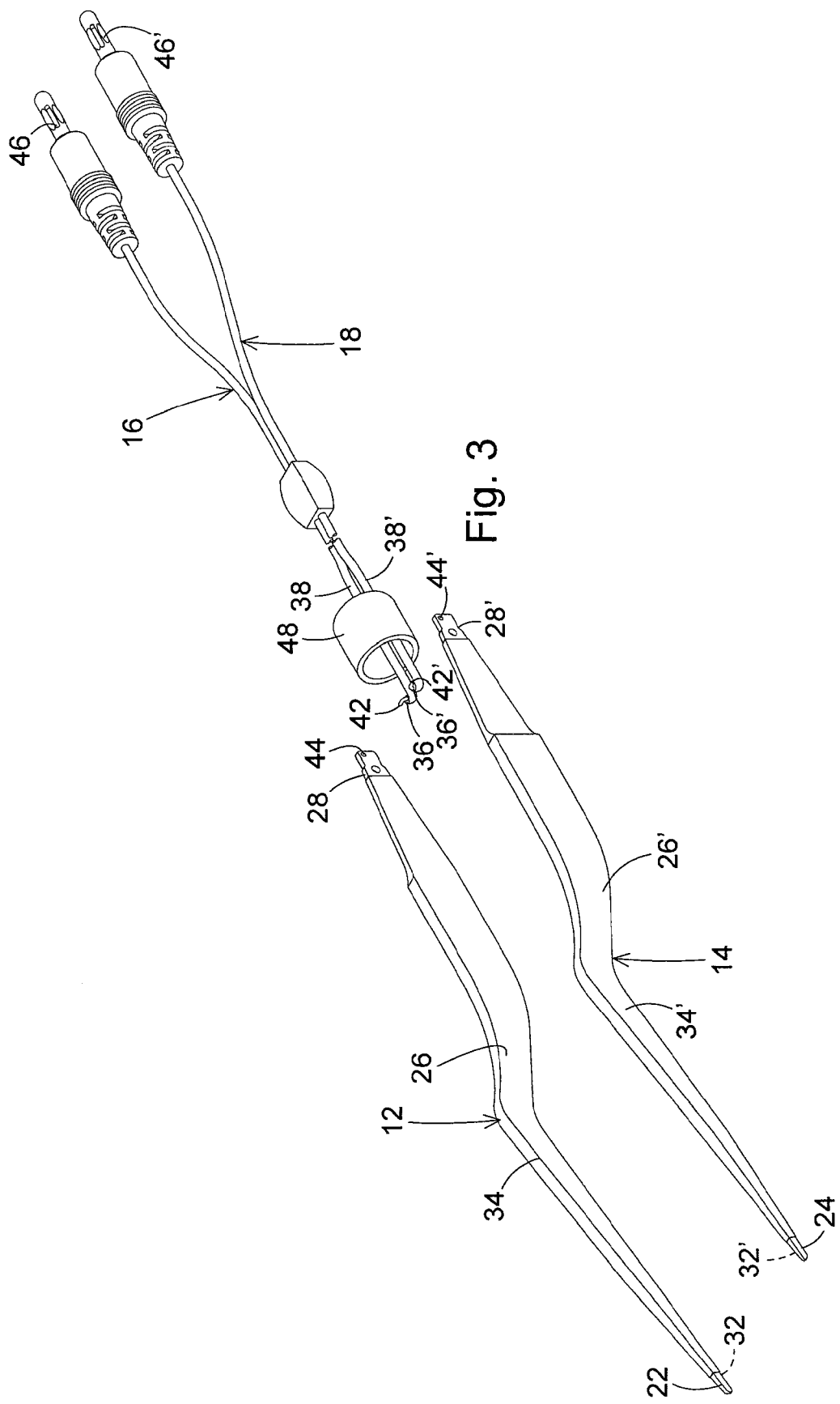

NON-STICK BIPOLAR FORCEPS

BACKGROUND OF THE INVENTION (1) Field of the Invention

The present invention pertains to disposable, bipolar electrosurgical forceps that are designed to prevent the sticking of body tissue to the tips of the forceps. More specifically, the present invention is directed to disposable, tissue-sticking resistant forceps that include a pair of electrode arms having lengths with opposite proximal and distal ends, with thin layers of biocompatible metal on the forceps arm distal ends and bipolar electrical conductors permanently secured to the forceps arm proximal ends. The manner in which the forceps are constructed enables the forceps to be manufactured inexpensively, and thereby enables the forceps to be disposable.

(2) Description of the Related Art

Bipolar electrosurgical forceps are typically constructed with a pair of electrode arms having proximal ends that are adapted to have electrical conductors removably attached to the proximal ends, and opposite distal ends with tips that contact and grasp or pinch body tissue between the tips during use of the forceps. For patient safety reasons, it is required that the portions of the forceps tips that contact the body tissue be constructed or formed of a biocompatible material that will not react with the body tissue. In the construction of prior art forceps, the biocompatible material commonly used on the tips of the forceps is an expensive metal such as stainless steel, titanium, tungsten and gold or silver. The use of this metal on the forceps tips is a significant factor in the manufacturing costs of the forceps.

In the use of prior art forceps, one of the electrical conductors connected to the forceps proximal end is connected to a source of electric power, and the other electrical conductor connected to the forceps proximal end is connected to a ground. The pair of forceps arms function as electrodes. When the forceps arms are manually manipulated by the surgeon to grasp body tissue between the distal end tips of the arms, an electric current is completed from one forceps arm through the body tissue to the other forceps arm. This current passing through the forceps tips and the body tissue heats the forceps tips and the body tissue held between the tips and causes the tissue to be joined or coagulated.

However, the heat produced in the forceps tips can also result in pieces of the body tissue sticking to the tips. During a surgical procedure using bipolar electrosurgical forceps, pieces of body tissue can accumulate on the forceps tips. As a result, sterilization of the forceps following the surgical procedure requires scrubbing or scraping of the forceps tips to remove the body tissue. This scrubbing and scraping of the tips can also result in a portion of the expensive biocompatible metal being removed from the tips. Over a period of time and after several uses and subsequent cleaning of the forceps, a sufficient amount of the biocompatible metal can be removed from the forceps tips to where the biocompatible material will no longer contact the body tissue in use of the instrument. At this point the instrument is no longer useful, requiring the disposal of the expensive instrument. This also requires the purchase of another expensive instrument to replace the disposed of instrument.

An additional disadvantage associated with reusable bipolar forceps having layers of biocompatible metals on the forceps tips is the potential for reducing the strength of the bond between the biocompatible metal layers and the forceps tips due to the cleaning of the forceps after each use. High temperature steam cleaning of the forceps can reduce the strength of the bond of the biocompatible metal with the forceps tips. This presents the potential of leaving foreign material in the body, for example in the brain, after a surgical procedure using the forceps. In addition, chemical cleaning of the forceps can adversely affect the forceps tip metal layers by a change in the chemical composition of the layers, for example tarnishing or oxidation of the tip layers.

To prolong the useful life of bipolar electrosurgical forceps, the thickness of the layer or amount of biocompatible metal at the forceps distal end tips has been increased. With the increased amount of biocompatible metal on the forceps distal end tips, the forceps can be used and sterilized a greater number of times before the biocompatible metal is worn away from the forceps tips by repeated sterilizations and scrubbing and scraping of the tips. However, due to the type of biocompatible metal (i.e., gold, silver, etc.) used on the forceps distal end tips, increasing the thickness of the metal significantly increases the cost of the surgical instrument.

To overcome these disadvantages of prior art bipolar electrosurgical forceps, what is needed is a novel construction of bipolar forceps that provides biocompatible metal at the forceps distal ends, but is constructed in a manner that reduces manufacturing costs and enables disposal of the forceps after one use.

SUMMARY OF THE INVENTION

The present invention provides a disposable, tissue-sticking resistant forceps. By being disposable, what is meant is that the forceps are specifically designed for one use in an electrosurgical procedure and for disposal after that one use.

The forceps are comprised of first and second elongate pincers. The pincers have the same configurations and are laser cut from a blank of aluminum and machined to their final configurations. Stamping, water jet cutting, EDM, plasma cutting, or molding processes could also be used to form the forceps pincers.

Electrical conductors are crimped to the distal ends of the pair of pincers. The pincers are secured together at their proximal ends, and the electrical conductors are secured to the pincers by a potting material that forms a base around the pincer proximal ends.

A layer of biocompatible metal, preferably silver, is applied to the distal end tips of the pair of pincers. To reduce manufacturing costs, the biocompatible metal has a thickness that is not more than 0.010 of an inch, and is preferably in a range of 0.002 to 0.005 of an inch. This significantly reduces the amount of the expensive biocompatible metal used in the construction of the forceps than that used in prior art forceps.

Constructing the forceps in this manner reduces their manufacturing costs and enables the forceps to be disposed of after a single use.

DESCRIPTION OF THE DRAWING FIGURES

Further features of the invention are set forth in the following detailed description of the preferred embodiment of the invention and in the drawing figures.

FIG. 1 is a side elevation view of the disposable forceps of the invention.

FIG. 2 is a top plan view of the forceps of FIG. 1.

FIG. 3 is a perspective assembly view of the forceps of FIG. 1.

DETAILED DESCRIPTION OF THE PREFERRED EMBODIMENT

Figure 4:
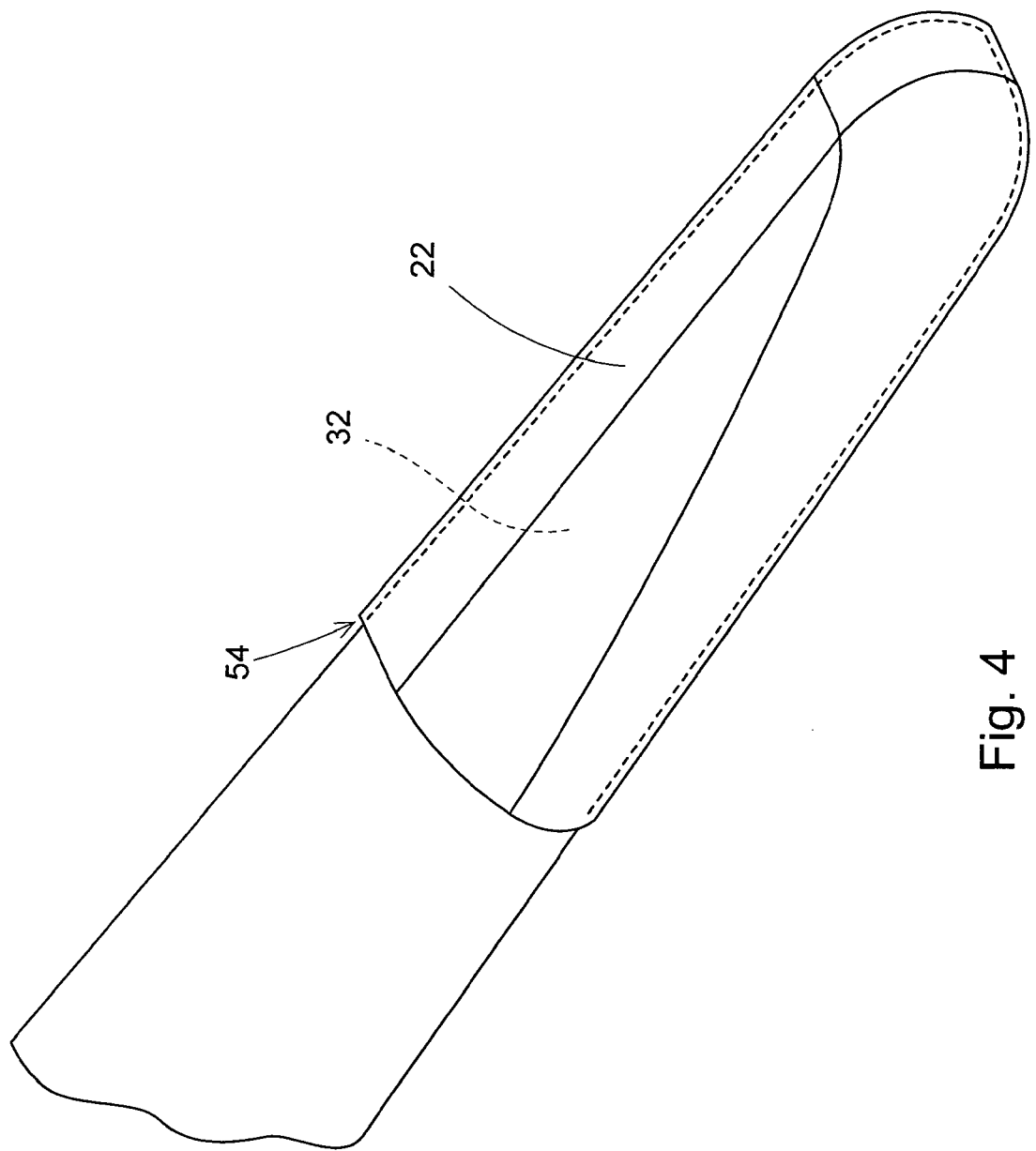
FIG. 4 is an enlarged partial view of the distal end of one of the forceps pincers.

FIGS. 1 and 2 show respective side and top views of the disposable, tissue sticking resistant, bipolar forceps of the present invention. The forceps are specifically designed to be disposable, bipolar electrosurgical forceps. In an alternate embodiment, the forceps could be designed as bipolar electrosurgical forceps having reusable electrode pincers with removable, disposable tips.

FIGS. 1-4 show the preferred embodiment of the forceps. This embodiment is basically comprised of a pair of forceps pincers or electrodes 12, 14, a pair of bipolar electrical conducting cords 16, 18, a base 20 that connects the pincers to each other and to the cords, and stick resistant tip layers 22, 24. As explained below, the construction of the forceps is simplified and comprises a minimum number of parts to reduce the manufacturing costs of the forceps and to make the disposal of the forceps after a single use economically feasible. Furthermore, as explained below, the use of expensive materials in the construction of the forceps is minimized to further reduce the manufacturing costs of the forceps and to make the disposal of the forceps economically feasible.

The first and second pincers 12, 14 of the forceps are constructed as mirror images of each other. In view of this, the construction of only the first pincer 12 is described in detail. The same reference numbers are employed to label the component parts of both pincers 12, 14, with the reference numbers of the second pincer 14 being followed by a prime ('). The pincer 12 is constructed with a narrow, elongate length having an intermediate portion 26 and opposite proximal 28 and distal 32 end portions. The pincer intermediate portion 26 is shaped and dimensioned to be held comfortably by a single hand of the surgeon using the forceps. In the preferred embodiment of the invention, the entire length of the pincer 12 is constructed from a blank of 6061-T6 aluminum that is laser cut to the configuration of the pincer shown. In alternate embodiments of the forceps, the pincers 12, 14 may be constructed entirely of stainless steel, entirely of brass, entirely of tin, entirely of copper, or entirely of an alloy of these materials. The pincers 12, 14 could also be constructed of a plastic material. However, a plastic embodiment of the pincers would require an electrical conductor extending the length of the pincers in order to enable the pincers to function as electrodes of the electrosurgical instrument. However, constructing the pincers entirely of aluminum is preferred over other materials to achieve the optimum non-stick perform of the forceps. This is largely due to the high thermal conductivity of the aluminum pincers.

An insulating coating 34 completely covers the intermediate portion 26 of the pincer 12. The coating 34 is electrically insulating, and may also be thermally insulating. The coating 34 covers only the intermediate portion 26 of the pincer 12, leaving the pincer proximal end portion 28 and the pincer distal end portion 32 projecting and exposed from the coating layer 34. A much thinner layer of the insulating coating 34 is applied to each pincer 12 of the disposable forceps than would be applied to pincers of a reusable forceps. Because the forceps are intended to be disposable, a thinner layer of the insulating coating may be used without concern for the layer wearing through during use. Applying the thinner layer of insulating coating 34 to the pincer 12 reduces the production cost, improves visual and sight access, and reduces the barrier for heat rejection to the environment imposed by a thicker insulating coating. The insulating coatings 34 primary purpose is to provide electrical insulation for the patient to prevent stray currents from damaging healthy tissue.

The first 16 and second 18 bipolar conducting cords are connected to the proximal ends 28, 28' of the first 12 and second 14 pincers. The two cords 16, 18 are identical in construction. Therefore, the construction of only the first cord 16 is described in detail. The same reference numbers employed in the description of the first cord 16 are also used in labeling the component parts of the second cord 18, but the reference numbers labeling the parts of the second cord 18 are followed by a prime ('). The construction of the first cord 16 is for the most part conventional. The cord contains an electrically conducting wire 36 that is covered by an insulator layer 38. A distal end 42 of the wire 36 extends from the insulator layer 38 and is electrically connected to the pincer proximal end 28. Referring to FIG. 3, the distal end 42 of the wire 36 is inserted through a hole 44 in the pincer proximal end 28 and crimped, thereby securing the cord 16 both mechanically and electrically to the pincer 12. The cord 16 has a flexible, elongate length that extends from the pincer 12 to an electrical connector 46 at the proximal end of the cord. The lengths of the cords 16, 18 allow the pincers 12, 14 to be easily manipulated by the hand of a surgeon when the electrical connectors, 46, 46' are connected to an electrical source. High strand count wire is used in the cord 16 for maximum flexibility. By crimping the wire 16 onto the pincer proximal end 28, the cost of a removable plug on the cord is eliminated, and also manufacturing difficulties associated in attaching a traditional connecting pin to the aluminum of the pincer 12 are overcome.

Providing integral electrical conductor cords on the forceps eliminates the cost of the electrical male plugs on the forceps and the removable conductor cords with female plug receptors of prior art bipolar forceps. This reduces the manufacturing cost of the forceps of the invention compared to that of prior art bipolar forceps.

The base 20 securely connects the pincer proximal ends 28, 28' together, and further secures the wire distal ends 42, 42' to the pincer proximal ends 28, 28'. The base is comprised of a cup shaped cap 48 having a hollow interior. A flexible electrically insulating material, preferably vinyl, is used in the construction of the cap. A pair of holes are provided in a bottom of the cup-shaped cap. The cords 16, 18 pass through the cap interior and holes and the cap 48 is positioned over the distal ends 42, 42' of the cord wires 36, 36' that have been crimped to the proximal ends 28, 28' of the pincers 12, 14. The interior of the cap 46 is potted with an epoxy material 52 that securely holds the pincers 12, 14 in their relative positions at the pincer proximal ends 28, 28', and securely holds the cords 16, 18 to the pincers. In this manner, the pincers 12, 14 and the cords 16, 18 are formed as an integral, disposable electrosurgical device. The cost of providing removable plug connectors between the forceps and the cords is eliminated. The cords 16, 16' originate at the bottom or back of the cap 48 (as held in the surgeon's hand) and naturally flow in the direction of the surgeon's arm to avoid creating any unwanted torque at the back of the forceps. In contrast, almost all reusable forceps have terminations that come straight out of the back of the forceps. When the cord is attached to a typical reusable forceps, the cord adversely affects the balance of the instrument in the surgeon's hand.

The first and second tip layers 22, 24 in the preferred embodiment of the invention are thin layers of biocompatible metal applied to the distal end portions 32, 32' of the pincers 12, 14. FIG. 4 shows the thin first layer of material 22 on the distal end tip 32 of the first pincer 12. The layer 24 on the second pincer 14 is the same as the first layer 22. In the preferred embodiment of the invention, the thickness 54 of the biocompatible material on the pincer distal ends 32, 32' is kept to a minimum to reduce costs, and is not more than 0.010 of an inch. More preferably, the thickness of the layer of biocompatible material on each pincer tip is not more than 0.005 of an inch, or is in a range of 0.0005 of an inch to 0.005 of an inch. The biocompatible material is preferably pure silver or pure gold. The thickness of 0.002 to 0.005 of an inch for the layer of biocompatible material is a specification for the silver plating process. Smaller thicknesses may also be acceptable, and the thickness range of 0.002 to 0.005 of an inch is chosen to be slightly more conservative in order to allow for some minor material removal when the tip layers are polished prior to packaging. It is possible that silver plating thicknesses as small as 0.0005 of an inch on aluminum, copper, or tungsten substrates may also provide non-stick performance.

The minimal thickness of the biocompatible metal on the pincer distal ends 32, 32' reduces the cost of materials used in the construction of the forceps, reduces the cost of manufacturing the forceps, and thereby enables the forceps to be disposable.

The disposable, tissue-sticking resistant forceps of the invention are used in the same manner as prior art bipolar electrosurgical forceps. However, once a single use of the forceps of the invention in a surgical procedure is completed, the forceps are disposed of and replaced with new forceps. Constructing the forceps with an identical pair of pincers laser cut from a metal blank, with integral electrical conductors or cords, and with a very thin layer of biocompatible metal on the forceps distal ends reduces the manufacturing costs of the forceps and enables the disposal of the forceps after a single use. An additional advantage of the disposable, integrated cord forceps is the convenience factor for ordering staff of a hospital or health clinic. Only one line item is needed to be ordered, with there being no concerns for ordering cords that are compatible with forceps for their interconnection. It is also convenient for surgical staff because the disposable, integrated cord design minimizes the parts on a sterile field, and is a convenience for cleaning staff by reducing the time required for autoclaving instruments and prolonging the useful life of cleaning equipment.

The pincers being constructed entirely of aluminum is critical to the operational success of the forceps. Aluminum alone may provide adequate non-stick performance for a brief time if concerns about biocompatibility were non existent and such an instrument was permitted in surgical procedures. However, after multiple coagulation hits, the aluminum tips would become oxidized and experience a significant reduction in electrical conductivity, thus the tips would almost become self insulting by their own oxide layer. Therefore, the silver or gold layered tips (non-oxidizing biocompatible materials) are employed as the coating layer on the aluminum forceps. The thermal properties of the silver, and also of gold layers are superior to aluminum. The tip layer thickness have been selected to provide excellent performance at low cost. The additional benefits provided by the aluminum construction of the pincers include low material costs, greater availability, high thermal conductivity, high thermal diffusivity, low heat retention, high electrical conductivity, very light weight, MRI compatible, adequate rigidity and strength, and non-toxic. No other materials employed in forceps constructions have the unique combinations of these characteristics.

The disposable, bipolar electrosurgical forceps of the invention have been described above by reference to specific embodiments of the forceps. It should be understood that modifications and variations could be made to the forceps described without departing from the intended scope of protection provided by the following claims.

What is claimed is:

1. Disposable, tissue sticking resistant forceps comprising:
first and second elongate pincers consisting of aluminum, each pincer having an intermediate body portion that is shaped and dimensioned to be held in a single hand, and each pincer having a proximal end portion and a distal end portion at opposite ends of the pincer body portion, the pincer proximal end portions being secured together, and the pincer distal end portions extending from the body portions to pointed end tips of the pincers;
an electrically conductive cord permanently connected to the proximal end portion of at least one pincer, the cord having a flexible length that extends from the at least one pincer to an electrical connector on an opposite end of the cord from the at least one pincer; and,
a layer of biocompatible metal on the aluminum of each pincer at only the pointed end tip, each layer of biocompatible metal consisting of a pure metal, each layer of biocompatible metal having a thickness that is less than 0.010 of an inch, thereby enabling the forceps to be disposable.

2. The forceps of claim 1, further comprising:
the thickness of the layer of biocompatible metal on each pincer pointed end tip being in a range of 0.0005 of an inch to 0.005 of an inch.

3. The forceps of claim 2, further comprising:
the biocompatible metal being pure silver.

4. The forceps of claim 2, further comprising:
the biocompatible metal being pure gold.

5. The forceps of claim 1, further comprising:
electrically insulating coatings over the intermediate body portions of the first and second pincers with the proximal end portions and the distal end portions of the first and second pincers being exposed from the coatings.

6. The forceps of claim 5, further comprising:
the electrically conductive cord being one cord of a pair of first and second electrically conductive cords having elongate, flexible lengths with opposite proximal and distal ends, the distal ends of the first and second cords being permanently secured to the respective proximal end portions of the first and second pincers and the proximal ends of the first and second cords having electrical connectors thereon.

7. The forceps of claim 6, further comprising:
a base of electrically insulating material encapsulating the proximal end portions of the first and second pincers and the distal ends of the first and second cords.

8. The forceps of claim 1, further comprising:
the layer of biocompatible metal on each pincer pointed end tip being not more than 0.005 of an inch.

9. Disposable, tissue sticking resistant forceps comprising:
first and second elongate pincers consisting of aluminum, each pincer having an intermediate body portion that is shaped and dimensioned to be held in a single hand, and each pincer having a proximal end portion and a distal end portion at opposite ends of the pincer body portion, the pincer proximal end portions being secured together;
first and second electrically conductive cords permanently secured to the proximal end portions of the respective first and second pincers, the first and second cords each having flexible lengths that extend from the first and second pincers to first and second electrical connectors on the respective first and second cords; and,
first and second tips on the distal end portions of the respective first and second pincers, each of the first and second tips consisting of a layer of a biocompatible metal on the aluminum at only the first and second tips of the pincers, where the layer of biocompatible metal has a thickness that is not more than 0.010 inches.

10. The forceps of claim 9, further comprising:
the thickness of the layer of biocompatible metal of each tip being in a range of 0.002 of an inch to 0.005 of an inch.

11. The forceps of claim 9, further comprising:
the biocompatible metal being pure silver.

12. The forceps of claim 9, further comprising:
the biocompatible metal being pure gold.

13. The forceps of claim 9, further comprising:
electrically insulating coatings over the intermediate body portions of the first and second pincers with the proximal end portions and the distal end portions of the first and second pincers being exposed from the coatings.

14. The forceps of claim 9, further comprising:
a base of electrically insulating material encapsulating the proximal end portions of the first and second pincers and the proximal ends of the first and second cords.

15. Disposable, tissue sticking resistant forceps comprising:
first and second elongate pincers consisting of aluminum, each pincer having an intermediate body portion that is shaped and dimensioned to be held in a single hand, and each pincer having a proximal end portion and a distal end portion at opposite ends of the pincer body portion;
coatings of electrically insulating material over the intermediate body portions of the first and second pincers;
a first electrically conductive cord connected to the proximal end portion of the first pincer;
a second electrically conductive cord connected to the proximal end of the second pincer;
a base of electrically insulating material encapsulating the proximal end portions of the first and second pincers and encapsulating portions of the first and second cords connected to the respective first and second pincers; and,
first and second layers consisting of biocompatible metal on the aluminum of only the distal end portions of the respective first and second pincers, the first and second layers of metal each having a thickness on the aluminum of the distal end portions of the respective first and second pincers of not more than 0.010 of an inch.

16. The forceps of claim 15, further comprising:
the first and second electrically conductive cords being bipolar cords that are permanently connected to the respective first and second pincers, the bipolar cords having flexible elongate lengths that extend from the pincers to electrical connectors at opposite ends of the cords lengths from the pincers.

17. The forceps of claim 16, further comprising:
the thickness of the layer of biocompatible material on each pincer tip being in a range of 0.002 of an inch to 0.005 of an inch.

* * * * *